United States Patent
Kwon et al.

(10) Patent No.: US 9,120,881 B2
(45) Date of Patent: Sep. 1, 2015

(54) LIGAND COMPOUND, CHROMIUM COMPOUND AND CATALYST SYSTEM INCLUDING THE SAME

(71) Applicant: LG CHEM, LTD., Seoul (KR)

(72) Inventors: Heon-Yong Kwon, Daejeon (KR); Yong-Ho Lee, Daejeon (KR); Kyoung-Chan Lim, Daejeon (KR); Ki-Soo Lee, Daejeon (KR); Min-Seok Cho, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/378,262

(22) PCT Filed: May 10, 2013

(86) PCT No.: PCT/KR2013/004158
§ 371 (c)(1),
(2) Date: Aug. 12, 2014

(87) PCT Pub. No.: WO2013/169068
PCT Pub. Date: Nov. 14, 2013

(65) Prior Publication Data
US 2015/0011382 A1    Jan. 8, 2015

(51) Int. Cl.
| | | |
|---|---|---|
| *C08F 4/78* | (2006.01) | |
| *C08F 4/52* | (2006.01) | |
| *C08F 110/02* | (2006.01) | |
| *B01J 31/16* | (2006.01) | |
| *C07F 11/00* | (2006.01) | |
| *C07F 7/10* | (2006.01) | |
| *C07F 7/20* | (2006.01) | |

(52) U.S. Cl.
CPC ............... *C08F 110/02* (2013.01); *B01J 31/16* (2013.01); *C07F 7/10* (2013.01); *C07F 7/20* (2013.01); *C07F 11/00* (2013.01); *C08F 4/52* (2013.01); *C08F 4/78* (2013.01)

(58) Field of Classification Search
None
See application file for complete search history.

(56) References Cited

U.S. PATENT DOCUMENTS

| 7,109,284 B2 | 9/2006 | Ishii et al. |
| 2011/0082325 A1 | 4/2011 | Suzuki et al. |

FOREIGN PATENT DOCUMENTS

| JP | 2011-518034 A | 6/2011 |
| KR | 10-2010-0087913 A | 8/2010 |
| KR | 10-2010-0088665 A | 8/2010 |
| KR | 10-2011-0000559 A | 1/2011 |
| KR | 10-2012-0048468 A | 5/2012 |
| WO | 03/053890 A1 | 7/2003 |
| WO | 2008004986 A1 | 1/2008 |

OTHER PUBLICATIONS

J. Zhang, et al., "Effect of Catalysts Supporting on Tandem Polymerization of Ethylene Stock in Synthesis of Ethylene-1-Hexene Copolymer", Ind. Eng. Chem. Res. 2008, 47, 5369-5375.
D. McGuinness, et al., "First Cr(III)-SNS Complexes and Their Use as Highly Efficient Catalysts for the Trimerization of Ethylene to 1-Hexene", J. Am. Chem. Soc. Communications, Feb. 19, 2003, 5272.
Gibson, V.C. et al., "Advances in Non-Metallocene Olefin Polymerization Catalysis", Chem. Rev., 2003, vol. 103, pp. 283-315.

*Primary Examiner* — Yun Qian
(74) *Attorney, Agent, or Firm* — Dentons US LLP

(57) ABSTRACT

The present invention relates to a ligand compound, a chromium compound, and a catalyst system including the same. The catalyst system including the ligand compound or chromium compound according to the present invention exhibits high catalytic activity in ethylene oligomerization reaction, and therefore, polyethylene can be prepared using a small amount of comonomers or using only ethylene without comonomers.

16 Claims, 1 Drawing Sheet

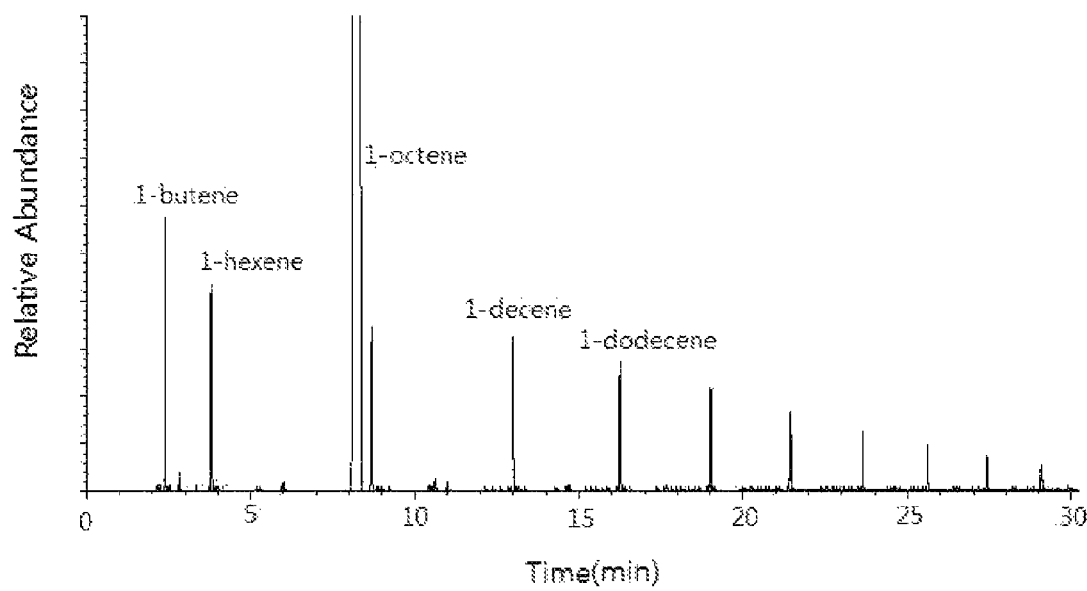

LIGAND COMPOUND, CHROMIUM COMPOUND AND CATALYST SYSTEM INCLUDING THE SAME

This application is a National Stage Application of International Patent Application No. PCT/KR2013/004158, filed on May 10, 2013, and claims the benefit of Korean Patent Application Nos. 10-2012-0049712, filed on May 10, 2012 and 10-2013-0052702, filed on May 9, 2013, in the Korean Intellectual Property Office, all of which are incorporated herein by reference in their entirety.

TECHNICAL FIELD

The present invention relates to a ligand compound, a chromium compound, and a catalyst system including the same. More particularly, the present invention relates to a novel ligand compound, chromium compound, and catalyst system including the same which exhibit high activity for ethylene oligomerization reaction.

This application claims the benefit of Korean Patent Application No. 10-2012-0049712 on May 10, 2012 and Korean Patent Application No. 10-2013-0052702 on May 9, 2013 with the Korean Intellectual Property Office, the disclosure of which is herein incorporated by reference in its entirety.

BACKGROUND ART

Linear alpha-olefin is widely used in important commercial substances such as comonomers, detergents, lubricants, plasticizers or the like, and in particular, 1-hexene and 1-octene are commonly used as comonomers for controlling density of polyethylene during preparation of linear low density polyethylene (LLDPE).

In the conventional preparation process of LLDPE (Linear Low-Density Polyethylene), copolymerization of ethylene with alpha-olefin, for example, a comonomer such as 1-hexene and 1-octene is carried out in order to control density by forming branches in the polymer backbone.

Therefore, there is a problem that the comonomer increases the production cost of LLDPE having a high content of comonomers. Many different methods have been tried to solve this problem.

Further, because the application field or market size depends on the type of alpha-olefin, a technique capable of selectively producing a particular olefin is commercially important. Recently, many studies have been conducted on a chromium catalyst for preparing 1-hexene or 1-octene with a high selectivity through selective ethylene oligomerization.

The conventional commercial method for 1-hexene or 1-octene preparation is the SHOP process of Shell Chemical, the Ziegler Process of Chevron Philips, or the like, which is used to produce alpha-olefins having a wide distribution range from C4~C20 carbons.

Further, many studies have been conducted to selectively prepare 1-hexene or 1-octene by ethylene trimerization or tetramerization using an organic metal catalyst (*J. Am. Chem. Soc* 2003, 125, 5272, *Ind. Eng. Chem. Res.* 2008, 47, 5369, WO03/053890), but there is a still need for the catalysts exhibiting a sufficiently high activity.

DISCLOSURE

Technical Problem

In order to solve the above problems of the conventional technology, an object of the present invention is to provide a novel ligand compound and chromium compound which maintain high activity and thus are used in ethylene oligomerization reaction so as to prepare low-density polyethylene in one reactor using a small amount of comonomers or using only ethylene without comonomers.

Further, another object of the present invention is to provide a catalyst system including the ligand compound or the chromium compound.

Technical Solution

In order to achieve the above objects, the present invention provides a ligand compound represented by the following Chemical Formula 1.

[Chemical Formula 1]

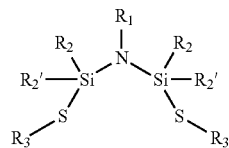

wherein $R_1$, $R_2$, $R_2'$ and $R_3$ are the same as or different from each other, and each independently a hydrogen atom, a hydrocarbyl group having 1 to 30 carbon atoms, or a heterohydrocarbyl group having 1 to 30 carbon atoms.

Further, the present invention provides a chromium compound represented by the following Chemical Formula 2.

[Chemical Formula 2]

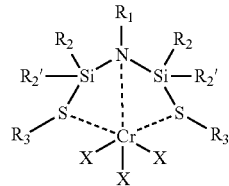

wherein $R_1$, $R_2$, $R_2'$ and $R_3$ are the same as or different from each other, and each independently a hydrogen atom, a hydrocarbyl group having 1 to 30 carbon atoms, or a heterohydrocarbyl group having 1 to 30 carbon atoms, and X is a halogen atom or an alkyl group having 1 to 6 carbon atoms.

Further, the present invention provides a catalyst system including i) the ligand compound represented by Chemical Formula 1 and a chromium source, or ii) the chromium compound represented by Chemical Formula 2; and a cocatalyst.

Advantageous Effects

The catalyst system including the ligand compound or the chromium compound according to the present invention can be used in ethylene oligomerization to oligomerize ethylene with a high catalytic activity, compared to the known catalyst system. That is, when a polyolefin is polymerized using the catalyst system according to the present invention, highly active ethylene oligomerization reaction is possible, and therefore, it is possible to polymerize a low-density polyethylene in one reactor using only ethylene without injection of additional comonomers.

DESCRIPTION OF DRAWINGS

FIG. 1 is a graph showing the result of GC-MS of the products resulting from ethylene oligomerization reaction according to Example 4 of the present invention.

BEST MODE

The terminology used herein is for the purpose of describing particular embodiments only and is not intended to be limiting of the invention. The singular forms are intended to include the plural forms as well, unless the context clearly indicates otherwise. It will be further understood that the terms "includes, "comprises," or "has" when used in this specification, specify the presence of stated features, integers, steps, components, or combinations thereof, but do not preclude the presence or addition of one or more other features, integers, steps, components, or combinations thereof.

While the present invention is susceptible to various modifications and alternative forms, specific embodiments thereof are shown by way of example and will herein be described in detail. It should be understood, however, that these are not intended to limit the invention to the particular form disclosed, but on the contrary, the intention is to cover all modifications, equivalents and alternatives falling within the spirit and scope of the present invention.

Hereinafter, a ligand compound, a chromium compound, and a catalyst system of the present invention will be described in detail.

Ligand Compound

The ligand compound of the present invention may be represented by the following Chemical Formula 1.

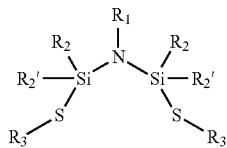

[Chemical Formula 1]

wherein $R_1$, $R_2$, $R_2'$ and $R_3$ are the same as or different from each other, and each independently a hydrogen atom, a hydrocarbyl group having 1 to 30 carbon atoms, or a heterohydrocarbyl group having 1 to 30 carbon atoms.

As used herein, the hydrocarbyl group means a monovalent hydrocarbon group, and the heterohydrocarbyl group means a monovalent heterohydrocarbon group containing carbon atom and one or more heteroatoms.

According to one embodiment of the present invention, $R_1$, $R_2$, $R_2'$ and $R_3$ are each independently a hydrogen atom, an alkyl group having 1 to 20 carbon atoms, an alkenyl group having 2 to 20 carbon atoms, an aryl group having 6 to 14 carbon atoms, an alkylaryl group having 7 to 12 carbon atoms, an arylalkyl group having 7 to 12 carbon atoms or an alkoxyaryl group having 7 to 12 carbon atoms, but are not limited thereto.

Preferably, $R_1$, $R_2$, $R_2'$ and $R_3$ are each independently a hydrogen atom, a linear alkyl group having 1 to 20 carbon atoms, an isopropyl group, a tert-butyl group, an amyl group, a phenyl group, an alkylphenyl group having 7 to 12 carbon atoms or an alkoxyphenyl group having 7 to 12 carbon atoms, but are not limited thereto.

According to one embodiment of the present invention, the compound represented by Chemical Formula 1 may be selected from the following chemical structures, but the present invention is not limited thereto.

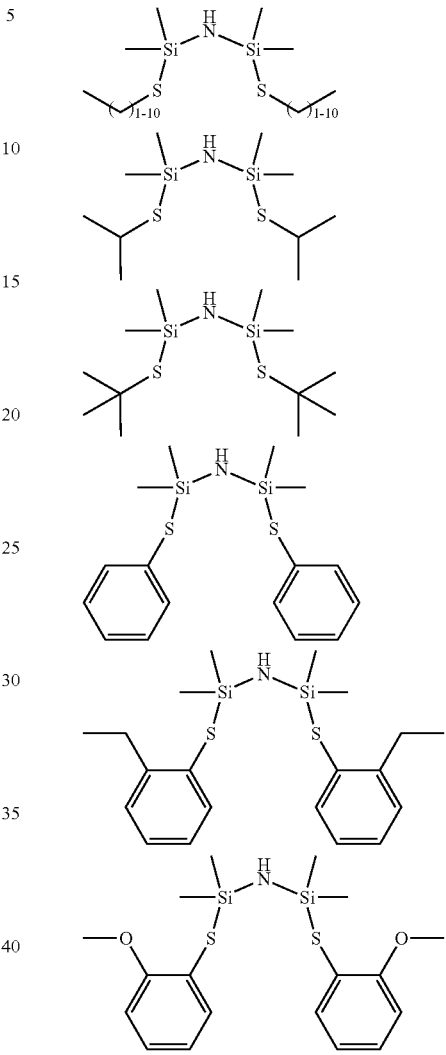

The compound represented by Chemical Formula 1 can be synthesized by the following method, but is not limited thereto. The preparation method of the ligand compound represented by Chemical Formula 1 will be described in detail in the following Examples.

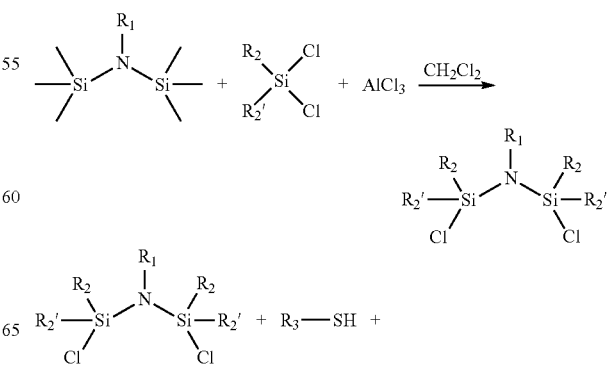

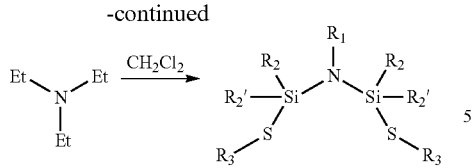

The ligand compound represented by Chemical Formula 1 may further include the chromium source and the cocatalyst to be used in ethylene oligomerization reaction. In particular, because highly active ethylene oligomerization reaction is possible, low-density polyethylene can be prepared in one reactor using a small amount of comonomers or using only ethylene without comonomers.

Chromium Compound

The chromium compound of the present invention may be represented by the following Chemical Formula 2.

[Chemical Formula 2]

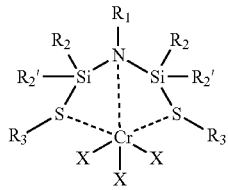

wherein $R_1$, $R_2$, $R_2'$ and $R_3$ are the same as or different from each other, and each independently a hydrogen atom, a hydrocarbyl group having 1 to 30 carbon atoms, or a heterohydrocarbyl group having 1 to 30 carbon atoms, and X is a halogen atom or an alkyl group having 1 to 6 carbon atoms.

Detailed descriptions and preferred examples of $R_1$, $R_2$, $R_2'$, and $R_3$ are the same as in the descriptions of the ligand compound of Chemical Formula 1.

In Chemical Formula 2, X is a halogen atom or an alkyl group having 1 to 6 carbon atoms, and specific examples thereof may include methyl, ethyl, propyl, isopropyl, t-butyl, iso-butyl or the like, but are not limited thereto.

According to one embodiment of the present invention, X is preferably Cl or a methyl group, and more preferably Cl.

According to one embodiment of the present invention, the chromium compound represented by Chemical Formula 2 may be selected from the following chemical structures, but the present invention is not limited thereto.

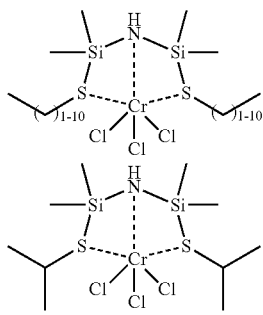

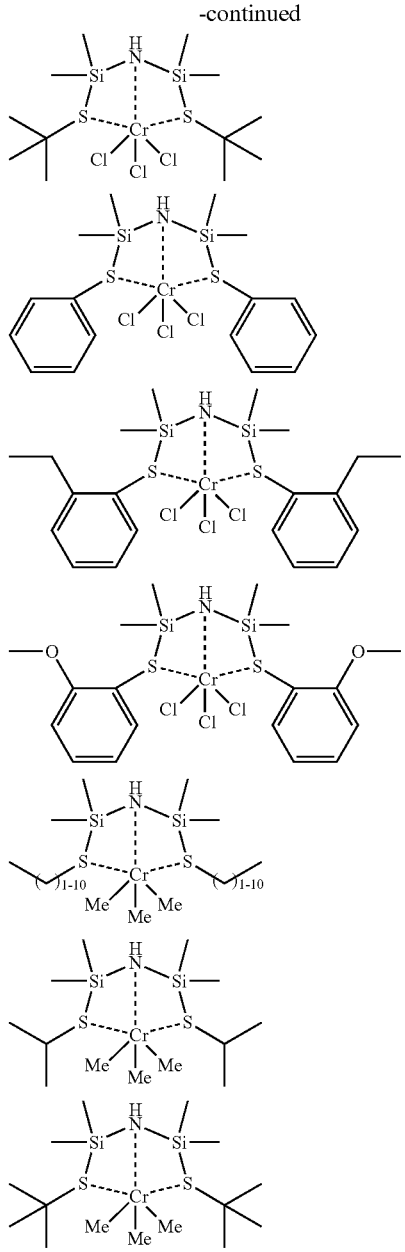

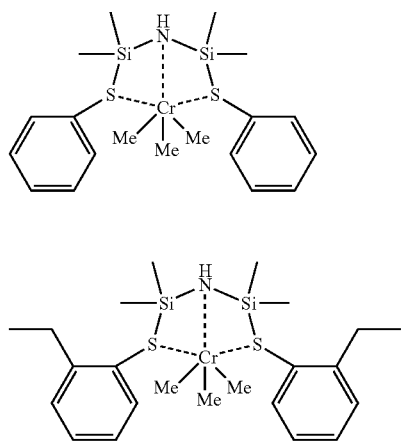

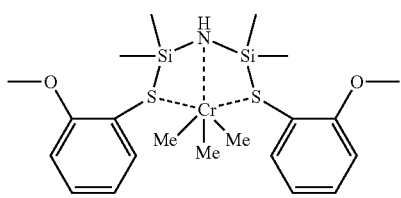

The chromium compound represented by Chemical Formula 2 can be synthesized by the following method, but is not limited thereto. The preparation method of the chromium compound represented by Chemical Formula 2 will be described in detail in the following Examples.

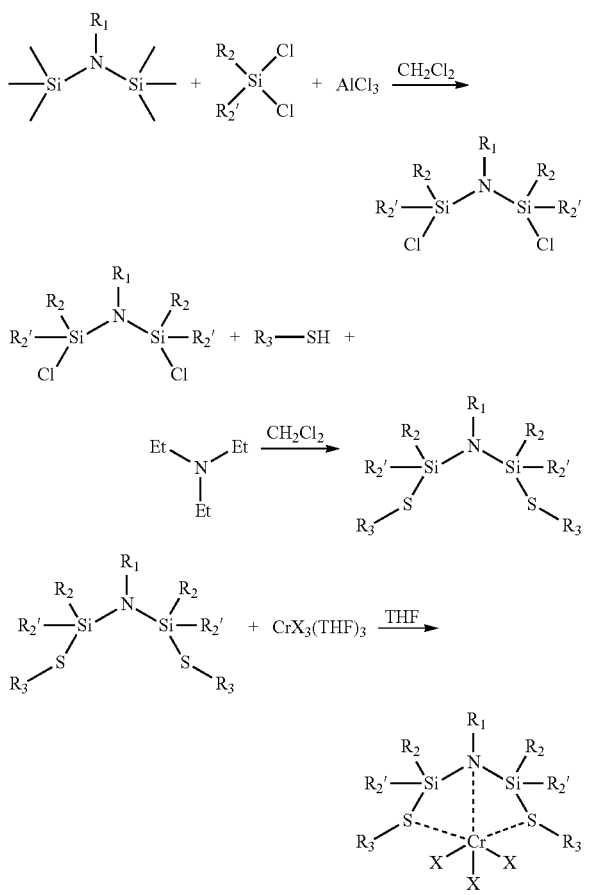

In ethylene oligomerization reaction, the chromium compound represented by Chemical Formula 2 may be used singly or as the catalyst system including the cocatalyst. In particular, because highly active ethylene oligomerization reaction is possible, low-density polyethylene can be prepared in one reactor using a small amount of comonomers or using only ethylene without comonomers.

Catalyst System

The catalyst system of the present invention includes i) a ligand compound represented by the following Chemical Formula 1 and a chromium source, or ii) a chromium compound represented by the following Chemical Formula 2; and a cocatalyst.

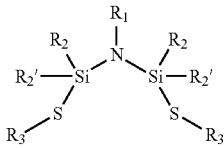

[Chemical Formula 1]

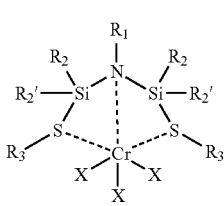

[Chemical Formula 2]

wherein $R_1$, $R_2$, $R_2'$ and $R_3$ are the same as or different from each other, and each independently a hydrogen atom, a hydrocarbyl group having 1 to 30 carbon atoms, or a heterohydrocarbyl group having 1 to 30 carbon atoms, and X is a halogen atom or an alkyl group having 1 to 6 carbon atoms.

Detailed descriptions and preferred examples of $R_1$, $R_2$, $R_2'$, $R_3$ and X of Chemical Formulae 1 and 2 are the same as in the descriptions of the ligand compound and the chromium compound of the present invention.

The catalyst system can be used in polymerization reaction of polyolefin, in particular, polyethylene, including ethylene oligomerization reaction.

As used herein, the term "catalyst system" means an active catalytic composition that can be obtained by adding three components of the chromium source, the ligand compound and the cocatalyst or alternatively two components of the chromium compound and the cocatalyst at the same time, or sequentially in any order in the presence or absence of any proper solvent in the presence or absence of monomers. The three components or two components of the catalyst system can be used without being supported on a support, or if necessary, they can be supported on the support to be used. That is, the catalyst system according to the present invention includes the ligand compound represented by Chemical Formula 1 and the chromium source, or the chromium compound represented by Chemical Formula 2 and the cocatalyst.

According to one embodiment of the present invention, the chromium source may be chromium or a chromium precursor. Specific examples of the chromium or chromium precursor may include chromium(III)acetylacetonoate, tris(tetrahydrofuran)chromium trichloride or chromium(III)-2-ethylhexanoate, but the present invention is not limited thereto.

In the catalyst system of the present invention, the cocatalyst may be an organic metal compound containing the Group 13 metal. The organic metal compound containing the Group 13 metal is not particularly limited, as long as it can be generally used in olefin polymerization in the presence of a catalyst of a transition metal compound.

Specifically, the cocatalyst may be one or more selected from the group consisting of the compounds represented by the following Chemical Formulae 3 to 5, but the present invention is not limited thereto.

—[Al($R_4$)—O]c-       [Chemical Formula 3]

wherein $R_4$ is the same as or different from each other, and each independently a halogen radical, a hydrocarbyl radical having 1 to 20 carbon atoms, a halogen-substituted hydrocarbyl radical having 1 to 20 carbon atoms, and c is an integer of 2 or more, $$D(R_5)_3 \quad \text{[Chemical Formula 4]}$$

wherein D is aluminium or boron, $R_5$ is hydrocarbyl having 1 to 20 carbon atoms or halogen-substituted hydrocarbyl having 1 to 20 carbon atoms, $$[L-H]^+[Q(E)_4]^- \quad \text{[Chemical Formula 5]}$$

wherein L is a neutral Lewis base, $[L-H]^+$ is a Bronsted acid, Q is boron or aluminium in the +3 oxidation state, E is each independently an aryl group having 6 to 20 carbon atoms or an alkyl group having 1 to 20 carbon atoms in which one or more hydrogen atoms are substituted or unsubstituted with halogen, hydrocarbyl having 1 to 20 carbon atoms, an alkoxy functional group or a phenoxy functional group.

Examples of the compound represented by Chemical Formula 3 may include methylaluminoxane (MAO), ethyl aluminoxane, isobutyl aluminoxane, butyl aluminoxane or the like.

Examples of the alkyl metal compound represented by Chemical Formula 4 may include trimethylaluminium, triethylaluminium, triisobutylaluminium, tripropylaluminium, tributylaluminium, dimethylchloroaluminium, dimethylisobutylaluminium, dimethylethylaluminium, diethylchloroaluminium, triisopropylaluminium, tri-s-butylaluminium, tricyclopentylaluminium, tripentylaluminium, triisopentylaluminium, trihexylaluminium, ethyldimethylaluminium, methyldiethylaluminium, triphenylaluminium, tri-p-tolylaluminium, dimethylaluminiummethoxide, dimethylaluminiumethoxide, trimethylboron, triethylboron, triisobutylboron, tripropylboron, tributylboron or the like.

Examples of the compound represented by Chemical Formula 5 may include triethylammoniumtetraphenylboron, tributylammoniumtetraphenylboron, trimethylammoniumtetraphenylboron, tripropylammoniumtetraphenylboron, trimethylammoniumtetra(p-tolyl)boron, tripropylammoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenyl boron, N,N-diethylaniliniumtetraphenylboron, N,N-diethylaniliniumtetrapentafluorophenylboron, diethylammoniumtetrapentafluorophenylboron, triphenylphosphoniumtetraphenylboron, trimethylphosphoniumtetraphenylboron, triethylammoniumtetraphenylaluminium, tributylammoniumtetraphenylaluminium, trimethylammoniumtetraphenylaluminium, tripropylammoniumtetraphenylaluminium, trimethylammoniumtetra(p-tolyl)aluminium, tripropylammoniumtetra(p-tolyl)aluminium, triethylammoniumtetra(o,p-dimethylphenyl)aluminium, tributylammoniumtetra(p-trifluoromethylphenyl)aluminium, trimethylammoniumtetra(p-trifluoromethylphenyl)aluminium, tributylammoniumtetrapentafluorophenylaluminium, N,N-diethylaniliniumtetraphenylaluminium, N,N-diethylaniliniumtetraphenylaluminium, N,N-diethylaniliniumtetrapentafluorophenylaluminium, diethylammoniumtetrapentafluorophenylaluminium, triphenylphosphoniumtetraphenylaluminium, trimethylphosphoniumtetraphenylaluminium, triphenylcarboniumtetraphenylboron, triphenylcarboniumtetraphenylaluminium, triphenylcarboniumtetra(p-trifluoromethylphenyl)boron, triphenylcarboniumtetrapentafluorophenylboron or the like.

According to one embodiment of the present invention, the cocatalyst may be alumoxane, and preferably, methyl alumoxane (MAO) as alumoxane.

According to one embodiment of the present invention, the catalyst system may include the ligand compound represented by Chemical Formula 1, the chromium source and the cocatalyst. In this regard, a molar ratio of ligand compound:chromium source:cocatalyst may be approximately 1:1:1 to approximately 10:1:10,000, and preferably, approximately 1:1:100 to approximately 5:1:3,000. When the amount of the cocatalyst is too small to be within the range, complete activation of the catalyst does not occur to reduce activity of the catalyst system. On the contrary, when an excessive amount of the cocatalyst is included, excessive activator is economically infeasible in terms of productivity or acts as impurities to reduce purity of the product.

The catalyst system including the ligand compound represented by Chemical Formula 1, the chromium source and the cocatalyst can be obtained as an active catalyst by adding three components of the catalyst system at the same time, or sequentially in any order in the presence or absence of monomers in any proper solvent. The proper solvent may include substituted or unsubstituted hydrocarbons having 4 to 12 carbon atoms, and examples thereof may include heptane, benzene, toluene, diethyl ether, tetrahydrofuran, acetonitrile, dichloromethane, chloroform, chlorobenzene or the like, but is not limited thereto.

According to another embodiment of the present invention, the catalyst system may include the chromium compound represented by Chemical Formula 2 and the cocatalyst. In this regard, the chromium compound represented by Chemical Formula 2 and the cocatalyst may be blended in a ratio of approximately 1:10 to approximately 1:10,000, and preferably, approximately 1:100 to approximately 1:1,000, based on the molar ratio of chromium and metal. When the amount of the cocatalyst is too small to be within the range, complete activation of the chromium compound does not occur to reduce activity of the catalyst system. On the contrary, when an excessive amount of the cocatalyst is included, excessive activator is economically infeasible in terms of productivity or acts as impurities to reduce purity of the product.

The catalyst system according to the present invention can be used in ethylene oligomerization reaction. That is, when ethylene oligomerization reaction or polyolefin polymerization reaction is carried out using the catalyst system according to the present invention, highly active ethylene oligomerization reaction is possible, and it is possible to polymerize low-density polyethylene in one reactor using only ethylene without additional injection of comonomers.

MODE FOR INVENTION

Hereinafter, the present invention will be described in more detail with reference to the following Examples. However, these Examples are illustrative purposes only, and the technical scope of the present invention is not limited thereto.

EXAMPLE

Synthesis of Ligand Compound and Chromium Compound

Example 1

Preparation of $\{CH_3CH_2-S-Si(Me)_2\text{-}NH-Si(Me)_2\text{-}S-CH_2CH_3\}CrCl_3$ [S-1 Complex]

Example 1-1

Preparation of 1,3-dichlorohexamethyldisilazane 15.2 g of Hexamethyldisilazane, 32.2 g of dichlorodimethylsilane, and 100 mg of $AlCl_3$ were added to a Schlenk flask, and 150 mL of dichloromethane was added as a solvent. The mixture was stirred at 50° C. for 3 days, and then the solvent was removed under vacuum. The crude product thus obtained was subjected to fractional distillation to give a colorless product. (Yield: 80%)

1H-NMR (500 MHz, $d_8$-benzene): δ(ppm) 1.10 (br, 1H), 0.28 (s, 12H)

Example 1-2

Preparation of $CH_3CH_2-S-Si(Me)_2\text{-}NH-Si(Me)_2\text{-}S-CH_2CH_3$ [S-1 Ligand]

1.06 g of 1,3-dichlorohexamethyldisilazane prepared in Example 1-1, 0.72 g of ethanethiol and 30 mL of THF were added to a Schlenk flask, and the mixture was cooled to −78° C. Next, 1.75 mL of triethylamine was slowly added, and the temperature was raised to room temperature. The mixture was stirred. After terminating the reaction, the solvent and volatile materials were removed under vacuum. 100 mL of hexane was added to a flask and then filtered through a filter frit, and hexane was removed under vacuum to give a light yellow liquid product. (Yield 95%)

1H-NMR (500 MHz, $CDCl_3$): δ(ppm) 2.56 (q, 4H), 1.30 (t, 6H), 0.39 (s, 12H)

Example 1-3

Preparation of $\{CH_3CH_2-S-Si(Me)_2\text{-}NH-Si(Me)_2\text{-}S-CH_2CH_3\}CrCl_3$ [S-1 Complex]

52 mg of $CH_3CH_2-S-Si(Me)_2\text{-}NH-Si(Me)_2\text{-}S-CH_2CH_3$ prepared in Example 1-2 and 77 mg of $CrCl_3(THF)_3$ were added to a Schlenk flask, and 50 mL of THF was added and stirred. The solvent was removed under vacuum to give the title compound as a light gray solid. (Yield 95%)

Example 2

Preparation of $\{CH_3(CH_2)_{10}-S-Si(Me)_2\text{-}NH-Si(Me)_2\text{-}S-(CH_2)_{10}CH_3\}CrCl_3$ [S-2 Complex]

Example 2-1

Preparation of $CH_3(CH_2)_{10}-S-Si(Me)_2\text{-}NH-Si(Me)_2\text{-}S-(CH_2)_{10}CH_3$ [S-2 Ligand]

1.06 g of 1,3-dichlorohexamethyldisilazane prepared in Example 1-1, 2.12 g of 1-dodecanethiol and 30 mL of THF were added to a Schlenk flask, and cooled to −78° C. Next, 1.75 mL of triethylamine was slowly added, and the temperature was raised to room temperature. Then, the mixture was stirred. After terminating the reaction, the solvent and volatile materials were removed under vacuum. 100 mL of hexane was added to a flask and then filtered through a filter frit, and hexane was removed under vacuum to give a light yellow liquid product. (Yield 93%)

1H-NMR (500 MHz, $CDCl_3$): δ(ppm) 2.57 (q, 4H), 1.56 (q, 4H), 1.35-1.20 (m, 32H), 0.86 (t, 6H), 0.40 (s, 12H)

Example 2-2

Preparation of $\{CH_3(CH_2)_{10}-S-Si(Me)_2\text{-}NH-Si(Me)_2\text{-}S-(CH_2)_{10}CH_3\}CrCl_3$ [S-2 Complex]

101 mg of $CH_3(CH_2)_{10}-S-Si(Me)_2\text{-}NH-Si(Me)_2\text{-}S-(CH_2)_{10}CH_3$ prepared in Example 2-1 and 60.9 mg of $CrCl_3(THF)_3$ were added to a Schlenk flask, 50 mL of THF was added thereto and stirred. The solvent was removed under vacuum to give the title compound as a light gray solid. (Yield 90%)

Example 3

Preparation of $\{(2\text{-MeO})C_6H_4-S-Si(Me)_2\text{-}NH-Si(Me)_2\text{-}S-C_6H_4(2\text{-OMe})\}CrCl_3$ [S-3 Complex]

Example 3-1

Preparation of $(2\text{-MeO})C_6H_4-S-Si(Me)_2\text{-}NH-Si(Me)_2\text{-}S-C_6H_4(2\text{-OMe})$ [S-3 Ligand]

The compound was prepared in the same manner as in Example 2-1, except using 2-methoxythiophenol instead of 1-dodecanethiol. (Yield 84%)

1H-NMR (500 MHz, $CDCl_3$): δ(ppm) 7.39 (q, 2H), 7.22 (q, 2H), 6.84 (m, 4H), 3.83 (s, 6H), 1.25 (brs, 1H), 0.25 (s, 12H)

Example 3-2

Preparation of $\{(2\text{-MeO})C_6H_4-S-Si(Me)_2\text{-}NH-Si(Me)_2\text{-}S-C_6H_4(2\text{-OMe})\}CrCl_3$ [S-3 Complex]

412 mg of $(2\text{-MeO})C_6H_4-S-Si(Me)_2\text{-}NH-Si(Me)_2\text{-}S-C_6H_4(2\text{-OMe})$ prepared in Example 3-1 and 377 mg of $CrCl_3(THF)_3$ were added to a Schlenk flask, and 20 mL of THF were added and stirred. The solvent was removed under vacuum to give the title compound as a light purple solid. (Yield 85%)

Comparative Example 1

Preparation of $\{CH_3CH_2-S-(CH_3)_2-NH-Si(CH_3)_2-S-CH_2CH_3\}CrCl_3$ [T Complex]

The title compound was prepared with reference to the previously reported literature, J. AM. CHEM. SOC. 2003, 125, 5272-5273.

<Ethylene Oligomerization Reaction>

Example 4

Ethylene Oligomerization Reaction of S-1 Complex

The pressure of 500 ml-high pressure reaction vessel was reduced to vacuum, and then the internal environment was made to inactive condition using argon gas. Then, 250 ml of pure toluene was added, and methylaluminoxane (MAO) was added 600-fold of the Al/Cr molar ratio. Subsequently, a toluene solution (5 ml, 25 μmol of S-1 complex) of 5 mM S-1 complex catalyst was added and the solution reaction was carried out at 60° C. for 1 hour under a 50 psig pressure of ethylene. Then, the activity was calculated from the increased weight of the solution after reaction and the weight of the reactor. The temperature of the reactor was reduced to 0° C., and then an HCl aqueous solution was slowly added to remove residual MAO and the catalyst. The organic layer was taken and filtered, and the produced polymer was separated and dried. Further, the organic layer was dried over $MgSO_4$ to remove the residual moisture, and then the composition of the organic layer was identified by GC-MS. As a result, a mixture of alpha-olefin polymers with Schultz-Flory distribution was identified.

A graph measured by GC-MS is shown in FIG. 1.

Example 5

Ethylene Oligomerization Reaction of S-1 Complex

Oligomerization reaction was carried out in the same manner as in Example 4, except that the reaction was carried out at a reaction temperature of 90° C. in Example 4.

Example 6

Ethylene Oligomerization Reaction of S-2 Complex

Oligomerization reaction was carried out in the same manner as in Example 4, except that S-2 complex was used instead of S-1 complex in Example 4.

Example 7

Ethylene Oligomerization Reaction of S-2 Complex

Oligomerization reaction was carried out in the same manner as in Example 4, except that S-2 complex was used instead of S-1 complex and the reaction was carried out at a reaction temperature of 90° C. in Example 4.

Example 8

Ethylene Oligomerization Reaction of S-3 Complex

Oligomerization reaction was carried out in the same manner as in Example 4, except that S-3 complex was used instead of S-1 complex in Example 4.

Example 9

Ethylene Oligomerization Reaction of S-3 Complex

Oligomerization reaction was carried out in the same manner as in Example 4, except that S-3 complex was used instead of S-1 complex and the reaction was carried out at a reaction temperature of 90° C. in Example 4.

Example 10

Ethylene Oligomerization Reaction using S-1 Ligand Compound and Chromium Source

The pressure of 500 ml-high pressure reaction vessel was reduced to vacuum, and then the internal environment was made to inactive condition using argon gas. Then, 250 ml of pure toluene was added, and methylaluminoxane (MAO) was added 600-fold of the Al/Cr molar ratio. Subsequently, a toluene solution (5 mM, 25 μmol) of 5 mM S-1 ligand compound of Example 1-2, 9.4 mg (25 μmol) of $CrCl_3(THF_3)$, and 5 mL of toluene were added to a 50 mL Schlenk flask, and stirred at room temperature for 5 minutes, and then added to a reactor. The solution reaction was carried out at 90° C. for 1 hour under a 50 psig pressure of ethylene. Then, the activity was calculated from the increased weight of the solution and the weight of the reactor. The temperature of the reactor was reduced to 0° C., and then an HCl aqueous solution was slowly added to remove residual MAO and the catalyst. The organic layer was taken and filtered, and the produced polymer was separated and dried. Further, the organic layer was dried over $MgSO_4$ to remove the residual moisture, and then the composition of the organic layer was identified by GC-MS. As a result, a mixture of alpha-olefin polymers with Schultz-Flory distribution was identified.

Example 11

Ethylene Oligomerization Reaction using S-2 Ligand Compound and Chromium Source

Oligomerization reaction was carried out in the same manner as in Example 10, except that S-2 ligand compound was used instead of S-1 ligand compound in Example 10.

Example 12

Ethylene Oligomerization Reaction using S-3 Ligand Compound and Chromium Source

Oligomerization reaction was carried out in the same manner as in Example 10, except that S-3 ligand compound was used instead of S-1 ligand compound in Example 10.

Comparative Example 2

Oligomerization reaction was carried out in the same manner as in Example 4, except that T complex of Comparative Example 1 was used instead of S-1 complex and the reaction was carried out at a reaction temperature of 90° C. in Example 4.

The results of ethylene oligomerization reaction of Examples 4 to 12 and Comparative Example 2 are shown in Table 1.

TABLE 1

| | Catalyst | Reaction temperature (unit: ° C.) | Activity (unit: g/g of Cr/hr) |
|---|---|---|---|
| Example 4 | S-1 complex | 60 | 13,850 |
| Example 5 | S-1 complex | 90 | 9,540 |
| Example 6 | S-2 complex | 60 | 29,160 |
| Example 7 | S-2 complex | 90 | 19,341 |
| Example 8 | S-3 complex | 60 | 7,615 |
| Example 9 | S-3 complex | 90 | 1,923 |
| Example 10 | S-1 ligand/chromium source | 90 | 9,120 |
| Example 11 | S-2 ligand/chromium source | 90 | 20,301 |
| Example 12 | S-3 ligand/chromium source | 90 | 1,510 |
| Comparative Example 2 | T complex | 90 | 2,510 |

Referring to Table 1, when ethylene oligomerization reaction was carried out using the catalyst system including the compound of the present invention, highly active ethylene oligomerization reaction was possible.

Referring to FIG. 1, when ethylene oligomerization reaction according to one embodiment of the present invention was carried out, it was found that alpha-olefin polymer products were obtained in the form of mixture according to Schultz-Flory distribution.

The invention claimed is:

1. A ligand compound represented by the following Chemical Formula 1:

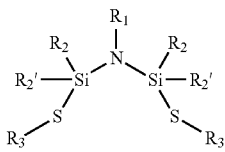

[Chemical Formula 1]

wherein $R_1$, $R_2$, $R_2'$ and $R_3$ are the same as or different from each other, and each independently a hydrogen atom, a hydrocarbyl group having 1 to 30 carbon atoms, or a heterohydrocarbyl group having 1 to 30 carbon atoms.

2. The ligand compound according to claim 1, wherein $R_1$, $R_2$, $R_2'$ and $R_3$ are each independently a hydrogen atom, an alkyl group having 1 to 20 carbon atoms, an alkenyl group having 2 to 20 carbon atoms, an aryl group having 6 to 14 carbon atoms, an alkylaryl group having 7 to 12 carbon atoms, an arylalkyl group having 7 to 12 carbon atoms or an alkoxyaryl group having 7 to 12 carbon atoms.

3. The ligand compound according to claim 1, wherein $R_1$, $R_2$, $R_2'$ and $R_3$ are each independently a hydrogen atom, a linear alkyl group having 1 to 20 carbon atoms, an isopropyl group, a tert-butyl group, an amyl group, a phenyl group, an alkylphenyl group having 7 to 12 carbon atoms or an alkoxyphenyl group having 7 to 12 carbon atoms.

4. The ligand compound according to claim 1, wherein the compound represented by Chemical Formula 1 is one of the following chemical structures:

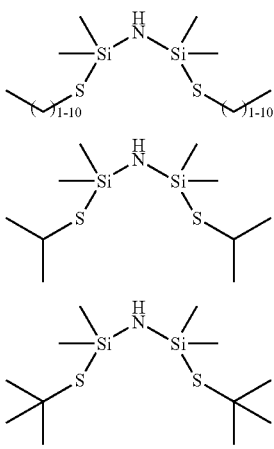

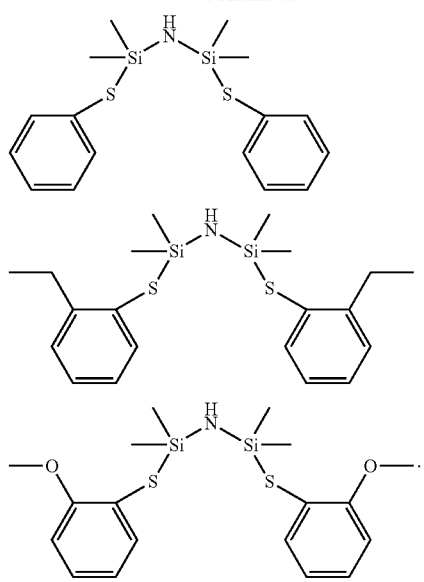

5. A chromium compound represented by the following Chemical Formula 2:

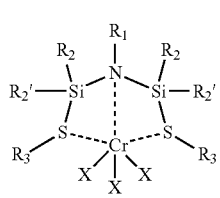

[Chemical Formula 2]

wherein $R_1$, $R_2$, $R_2'$ and $R_3$ are the same as or different from each other, and each independently a hydrogen atom, a hydrocarbyl group having 1 to 30 carbon atoms, or a heterohydrocarbyl group having 1 to 30 carbon atoms, and X is a halogen atom or an alkyl group having 1 to 6 carbon atoms.

6. The chromium compound according to claim 5, wherein $R_1$, $R_2$, $R_2'$ and $R_3$ are each independently a hydrogen atom, an alkyl group having 1 to 20 carbon atoms, an alkenyl group having 2 to 20 carbon atoms, an aryl group having 6 to 14 carbon atoms, an alkylaryl group having 7 to 12 carbon atoms, an arylalkyl group having 7 to 12 carbon atoms or an alkoxyaryl group having 7 to 12 carbon atoms.

7. The chromium compound according to claim 5, wherein $R_1$, $R_2$, $R_2'$ and $R_3$ are each independently a hydrogen atom, a linear alkyl group having 1 to 20 carbon atoms, an isopropyl group, a tert-butyl group, an amyl group, a phenyl group, an alkylphenyl group having 7 to 12 carbon atoms or an alkoxyphenyl group having 7 to 12 carbon atoms.

8. The chromium compound according to claim 5, wherein X is Cl or a methyl group.

9. The chromium compound according to claim 5, wherein the compound represented by Chemical Formula 2 is one of the following chemical structures:

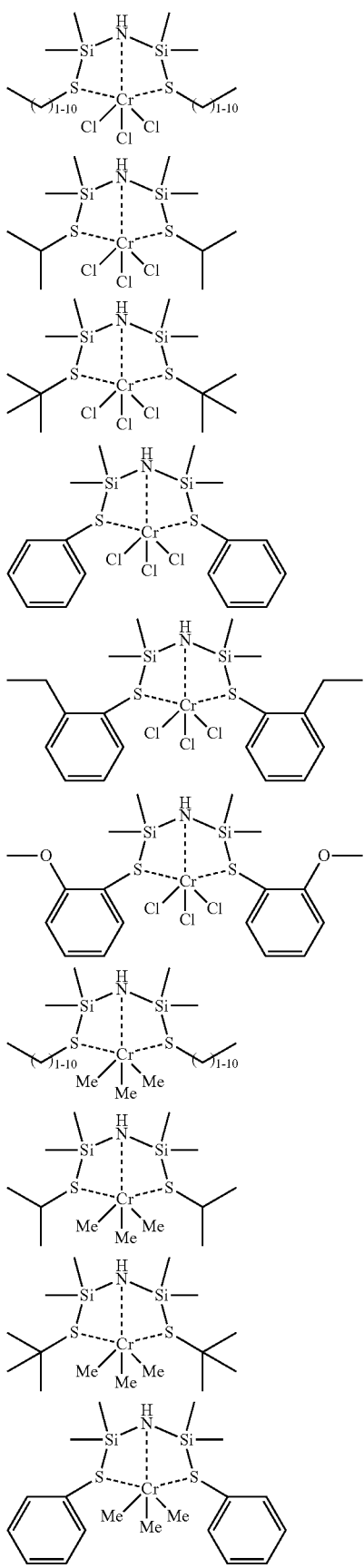

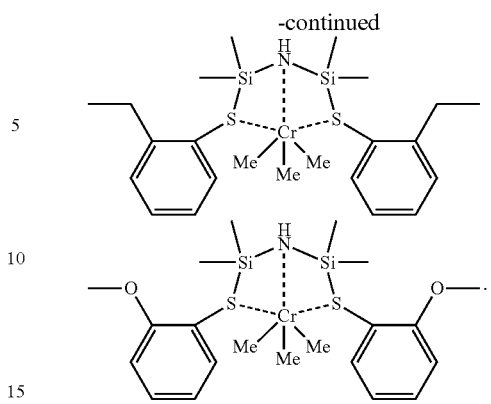

10. A catalyst system comprising i) a ligand compound represented by the following Chemical Formula 1 and a chromium source, or ii) a chromium compound represented by the following Chemical Formula 2; and a cocatalyst:

[Chemical Formula 1]

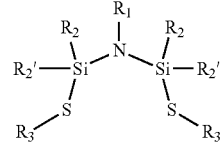

[Chemical Formula 2]

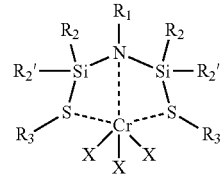

wherein $R_1$, $R_2$, $R_2'$ and $R_3$ are the same as or different from each other, and each independently a hydrogen atom, a hydrocarbyl group having 1 to 30 carbon atoms, or a heterohydrocarbyl group having 1 to 30 carbon atoms, and X is a halogen atom or an alkyl group having 1 to 6 carbon atoms.

11. The catalyst system according to claim 10, wherein $R_1$, $R_2$, $R_2'$ and $R_3$ are each independently a hydrogen atom, an alkyl group having 1 to 20 carbon atoms, an alkenyl group having 2 to 20 carbon atoms, an aryl group having 6 to 14 carbon atoms, an alkylaryl group having 7 to 12 carbon atoms, an arylalkyl group having 7 to 12 carbon atoms or an alkoxyaryl group having 7 to 12 carbon atoms.

12. The catalyst system according to claim 10, wherein $R_1$, $R_2$, $R_2'$ and $R_3$ are each independently a hydrogen atom, a linear alkyl group having 1 to 20 carbon atoms, an isopropyl group, a tert-butyl group, an amyl group, a phenyl group, an alkylphenyl group having 7 to 12 carbon atoms or an alkoxyphenyl group having 7 to 12 carbon atoms.

13. The catalyst system according to claim 10, wherein X is Cl or a methyl group.

14. The catalyst system according to claim 10, wherein chromium source is selected from the group consisting of chromium(III)acetylacetonoate, tris(tetrahydrofuran)chromium trichloride, and chromium(III)-2-ethylhexanoate.

15. The catalyst system according to claim 10, wherein the cocatalyst is one or more selected from the group consisting of the compounds represented by the following Chemical Formulae 3 to 5:

—[Al(R_4)—O]c-  [Chemical Formula 3]

wherein $R_4$ is the same as or different from each other, and each independently a halogen radical, a hydrocarbyl radical having 1 to 20 carbon atoms, a halogen-substituted hydrocarbyl radical having 1 to 20 carbon atoms, and c is an integer of 2 or more, $$D(R_5)_3 \quad \text{[Chemical Formula 4]}$$

wherein D is aluminium or boron, $R_5$ is hydrocarbyl having 1 to 20 carbon atoms or halogen-substituted hydrocarbyl having 1 to 20 carbon atoms, $$[L\text{-}H]^+[Q(E)_4]^- \quad \text{[Chemical Formula 5]}$$

wherein L is a neutral Lewis base, $[L\text{-}H]^+$ is a Bronsted acid, Q is boron or aluminium in the +3 oxidation state, E is each independently an aryl group having 6 to 20 carbon atoms or an alkyl group having 1 to 20 carbon atoms in which one or more hydrogen atoms are substituted or unsubstituted with halogen, hydrocarbyl having 1 to 20 carbon atoms, an alkoxy functional group or a phenoxy functional group.

16. The catalyst system according to claim 10, wherein the catalyst system is used in ethylene oligomerization reaction.

* * * * *